US008624021B2

(12) United States Patent
Sugimoto et al.

(10) Patent No.: US 8,624,021 B2
(45) Date of Patent: Jan. 7, 2014

(54) COMPOUND AND PROCESS FOR PRODUCING AMIDE COMPOUND THEREWITH

(75) Inventors: Tsunemi Sugimoto, Ube-she (JP); Mitsuru Kishishita, Ube (JP); Junichi Kugimoto, Ube (JP); Kazunori Kurosawa, Ube (JP); Hideo Shimomura, Ube (JP); Ryouta Yasumatsu, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 26 days.

(21) Appl. No.: 13/497,687

(22) PCT Filed: Sep. 24, 2010

(86) PCT No.: PCT/JP2010/066600
§ 371 (c)(1),
(2), (4) Date: Mar. 22, 2012

(87) PCT Pub. No.: WO2011/037208
PCT Pub. Date: Mar. 31, 2011

(65) Prior Publication Data
US 2013/0005961 A1   Jan. 3, 2013

(30) Foreign Application Priority Data

| Sep. 24, 2009 | (JP) | 2009-218739 |
| Nov. 4, 2009 | (JP) | 2009-253254 |
| Nov. 6, 2009 | (JP) | 2009-254583 |
| Nov. 16, 2009 | (JP) | 2009-260866 |
| Dec. 9, 2009 | (JP) | 2009-279079 |
| Jul. 30, 2010 | (JP) | 2010-172406 |

(51) Int. Cl.
*C07D 225/02* (2006.01)
*C07D 201/04* (2006.01)

(52) U.S. Cl.
USPC ............................................................ 540/464

(58) Field of Classification Search
USPC ............................................................ 540/464
See application file for complete search history.

(56) References Cited

U.S. PATENT DOCUMENTS

| 3,431,255 A | 3/1969 | Strauss et al. |
| 3,755,162 A | 8/1973 | Schultz et al. |
| 3,825,532 A | 7/1974 | Kern et al. |
| 5,254,684 A | 10/1993 | Izumi et al. |
| 2010/0029932 A1 | 2/2010 | Ishii et al. |

FOREIGN PATENT DOCUMENTS

| EP | 0487090 A2 | 5/1992 |
| EP | 2 404 900 A1 | 1/2012 |
| GB | 1 467 565 | 3/1977 |
| JP | A-S47-12870 | 6/1972 |
| JP | A-S51-41376 | 4/1976 |
| JP | B-S51-46109 | 12/1976 |
| JP | B-S52-12198 | 4/1977 |
| JP | B-1977-033118 | 8/1977 |
| JP | A-H04-342570 | 11/1992 |
| JP | A-H05-4964 | 1/1993 |
| JP | A-H05-105654 | 4/1993 |
| JP | A-2001-302602 | 10/2001 |
| JP | A-2001-302603 | 10/2001 |
| JP | A-2003-128638 | 5/2003 |
| JP | A-2004-059553 | 2/2004 |
| JP | A-2006-56811 | 3/2006 |
| JP | A-2006-219470 | 8/2006 |
| JP | A-2008-162935 | 7/2008 |
| WO | WO 2010/101229 A1 | 9/2010 |

OTHER PUBLICATIONS

International Preliminary Report on Patentability issued in corresponding International Patent Application No. PCT/JP2010/066600 on Apr. 11, 2012.
Written Opinion issued in corresponding International Patent Application No. PCT/JP2010/066600 mailed Dec. 21, 2010.
International Search Report issued in corresponding International Patent Application No. PCT/JP2010/066600 on Dec. 21, 2010.
Shrestha-Dawadi et al., "Meerwein's Catalytic Beckmann Rearrangement," Journal für praktische Chemie Chemiker-Zeitung, vol. 338, pp. 460-467, 1996.
Extended European Search Report issued in European Patent Application No. 10818880.6 on Mar. 12, 2013.
Office Action issued on May 2, 2013 in Chinese Patent Application No. 201080053264.3.

*Primary Examiner* — Bruck Kifle
(74) *Attorney, Agent, or Firm* — Knobbe Martens Olson & Bear LLP

(57) ABSTRACT

The present invention provides novel cyclododecanone-O-azacyclotridecen-2-yloxime and cyclododecanone-O-azacyclotridecen-2-yloxime hydrochloride. The invention also provides a process for producing an amide compound wherein cyclododecanone-O-azacyclotridecen-2-yloxime, hydrogen chloride and/or Lewis acid or cyclododecanone-O-azacyclotridecen-2-yloxime hydrochloride are used as a rearrangement catalyst and/or a reaction starting material in a reaction step.

14 Claims, No Drawings

COMPOUND AND PROCESS FOR PRODUCING AMIDE COMPOUND THEREWITH

This application is the U.S. National Phase under 35 U.S.C. §371 of International Application No. PCT/JP2010/066600, filed Sep. 24, 2010, designating the U.S., and published in Japanese as WO2011/037208 on Mar. 31, 2011, which claims priority to Japanese Patent Application No. 2009-218739, filed Sep. 24, 2009; Japanese Patent Application No. 2009-253254, filed Nov. 4, 2009; Japanese Patent Application No. 2009-254583, filed Nov. 6, 2009; Japanese Patent Application No. 2009-260866, filed Nov. 16, 2009; Japanese Patent Application No. 2009-279079, filed Dec. 9, 2009; and Japanese Patent Application No. 2010-172406, filed Jul. 30, 2010, the entire contents of which are incorporated herein by reference.

TECHNICAL FIELD

The present invention relates to a process for producing an amide compound by Beckmann rearrangement of an oxime compound. In particular, the invention relates to a process for producing an amide compound such as laurolactam useful as a starting material for Nylon 12 using cyclododecanone-O-azacyclotridecen-2-yloxime or hydrochloride thereof.

BACKGROUND OF THE INVENTION

An industrial production of laurolactam by Beckmann rearrangement reaction of cyclododecanone oxime generally employs concentrated sulfuric acid or oleum as a rearranging agent. However, it is necessary to use sulfuric acid in an equimolar amount to the oxime and to, after the reaction, neutralize sulfuric acid with a base such as ammonia, which causes that a large amount of ammonium sulfate is formed as a byproduct. The process, therefore, requires facilities for producing concentrated sulfuric acid and oleum and for treating ammonium sulfate, which is a process with significant environmental burden and facility cost (Patent Document No. 1, Patent Document No. 2).

For solving such a problem, various catalyst reaction systems have been investigated. For example, there have been described Beckmann rearrangement reaction using cyanuric chloride as a catalyst (see Patent Document 3 and Non-patent Document 1), rearrangement of the oxime in the presence of a dialkylamide compound and phosphorous pentoxide (see Patent Document 4), rearrangement of the oxime in the presence of a dialkylamide compound, phosphorous pentoxide and a fluorine-containing strong acid (see Patent Document 5), rearrangement of the oxime in the presence of a dialkylamide compound, a condensed phosphoric acid compound and optionally a fluorine-containing strong acid (see Patent Document 6), rearrangement of the oxime in the presence of a dialkylamide compound, phosphorous pentoxide or a condensed phosphoric acid compound, and a non-fluorinated sulfonic anhydride (see Patent Document 7), rearrangement of the oxime in the presence of a dialkylamide compound, an inorganic acid and a carboxylic anhydride (see Patent Document 8), and rearrangement of the oxime in the presence of an acid anhydride under the condition that the total molar amount of water contained in a reaction system is 15 or less to that of the acid anhydride (see Patent Document 9). However, most of the processes employ a particular catalyst or solvent for which a recovering or recycling method has not been explicitly described and are thus imperfect as an industrial process.

Those that are relatively inexpensive and readily available as industrial chemicals include cyanuric chloride, phosphorous trichloride, phosphorous pentachloride and thionyl chloride. Among these, cyanuric chloride, phosphorous trichloride and phosphorous pentachloride are converted, when inactivated, into compounds insoluble in an organic solvent such as cyanuric acid and phosphoric acid, and therefore when being used in a large amount, they cause pipe blockage or poor heat transfer in an industrial process, and thus they are undesirable. In contrast, since thionyl chloride is finally decomposed to generate hydrogen chloride and sulfur dioxide without solid precipitation, a simple industrial process can be formed.

In terms of Beckmann rearrangement of an oxime compound using thionyl chloride as a catalyst, Patent Document Nos. 11 and 12 have disclosed a process wherein a mixture of thionyl chloride and an oxime compound is heated. It has been, however, found that in the process, a yield varies depending on, for example, a temperature-increase rate and a yield itself is low. In addition, Beckmann rearrangement is a severely exothermic reaction, which cannot be controlled by the process described in Patent Document Nos. 11 and 12 and cannot be expanded to an industrial scale. Furthermore, a process in which thionyl chloride is added to a solution of an oxime compound heated to a predetermined temperature does not provide a target amide compound in a good yield. Therefore, further improvement is required.

PATENT DOCUMENTS

Patent Document No. 1: Japanese Examined Patent Publication No. 1977-033118.
Patent Document No. 2: Japanese Laid-open Patent Publication No. 1993-4964.
Patent Document No. 3: Japanese Laid-open Patent Publication No. 2006-219470.
Patent Document No. 4: Japanese Laid-open Patent Publication No. 1992-342570.
Patent Document No. 5: Japanese Laid-open Patent Publication No. 1993-105654.
Patent Document No. 6: Japanese Laid-open Patent Publication No. 2001-302602.
Patent Document No. 7: Japanese Laid-open Patent Publication No. 2001-302603.
Patent Document No. 8: Japanese Laid-open Patent Publication No. 2003-128638.
Patent Document No. 9: Japanese Laid-open Patent Publication No. 2004-59553.
Patent Document No. 10: Japanese Examined Patent Publication No. 1976-46109.
Patent Document No. 11: Japanese Laid-open Patent Publication No. 1976-041376.
Patent Document No. 12: Japanese Examined Patent Publication No. 1977-012198.

NON-PATENT DOCUMENTS

Non-patent Document No. 1: Journal of American Chemical Society, pp. 11240 (2005).

Problem to be Solved by the Invention

An objective of the present invention is to provide a process for producing an amide compound by Beckmann rearrangement of an oxime compound wherein an inexpensive catalyst resistant to decomposition precipitation is used without generating ammonium sulfate as a byproduct. Another objective of the invention is to provide an industrially suitable process for producing an amide compound whereby a desired amide compound can be produced in a high yield using a small amount of a catalyst as well as a preparation process for such a catalyst.

A further objective of the present invention is to provide a novel compound to be a highly active catalyst generating a less amount of byproducts and exhibiting good handling properties which is used in a process for producing an amide compound, as well as a novel production process using the compound.

Means for Solving Problem

The present invention relates to the following items.
1. Cyclododecanone-O-azacyclotridecen-2-yloxime represented by the following formula, its stereoisomer or a mixture thereof.

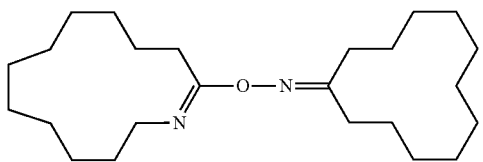 [SMILES: C1CCCCCC(=NO/C2=N/CCCCCCCCCCC2)CCCCC1]

2. Cyclododecanone-O-azacyclotridecen-2-yloxime hydrochloride represented by the following formula, its stereoisomer or a mixture thereof.

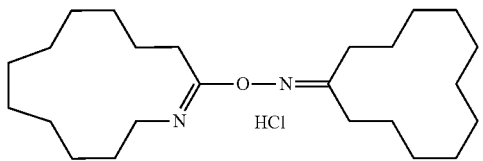

3. A process for producing an amide compound comprising:
   blending
   (i) cyclododecanone-O-azacyclotridecen-2-yloxime and
   (ii) hydrogen chloride and/or Lewis acid, and
   providing the mixture as a Beckmann rearrangement catalyst and/or a reaction starting material in a reaction step.
4. The process according to the above item 3, wherein when hydrogen chloride and a Lewis acid are used, the Lewis acid is halides of one or two or more metals selected from the group consisting of zinc, cobalt, antimony, tin and bismuth.
5. The process according to the above item 3, wherein when hydrogen chloride is absent and a Lewis acid is used, the Lewis acid is halides of tin and/or bismuth.
6. A process for producing an amide compound comprising providing cyclododecanone-O-azacyclotridecen-2-yloxime hydrochloride as a Beckmann rearrangement catalyst and/or a reaction starting material in a reaction step.
7. The process according to the above item 6, further using a Lewis acid.
8. The process according to the above item 7, wherein the Lewis acid is halides of one or two or more metals selected from the group consisting of zinc, cobalt, antimony, tin and bismuth.
9. A process for producing cyclododecanone-O-azacyclotridecen-2-yloxime, comprising:
   blending and dissolving thionyl chloride and cyclododecanone oxime in a two molar amount to thionyl chloride in the presence of a solvent,
   evaporating the solvent,
   adding a solvent again and washing the resulting solution with an aqueous alkaline solution until an aqueous layer becomes alkaline.
10. A process for producing cyclododecanone-O-azacyclotridecen-2-yloxime hydrochloride comprising:
    blending and dissolving thionyl chloride and cyclododecanone oxime in a two molar amount to thionyl chloride in the presence of a solvent, and
    evaporating the solvent.
11. A process for producing an amide compound by a Beckmann rearrangement reaction of an oxime compound using thionyl chloride in a continuous flow apparatus, the process comprising pre-preparation step wherein the oxime compound and thionyl chloride are blended and reacted to form a chlorine-containing catalytically active species.
12. The process according to the above item 11, wherein the apparatus used in the pre-preparation step comprises three parts consisting of a mixing unit, a pipe for a mixed liquid and a degassing tank,
    wherein the oxime compound and thionyl chloride are blended and reacted in the mixing unit, and a gas generated in the reaction is degassed in the degassing tank.
13. The process according to the above item 11 or 12, wherein in the pre-preparation step, a molar ratio of the oxime compound to thionyl chloride is 2 or more.
14. The process according to any one of the above items 11 to 13, wherein a reaction temperature during the pre-preparation step is a temperature of the Beckmann rearrangement reaction or lower.

Advantage of the Invention

According to the present invention, an inexpensive and industrially available rearrangement catalyst can be used in a process for producing an amide compound by Beckmann rearrangement of an oxime compound whereby the reaction can be completed with a small amount of the catalyst. Furthermore, the present invention allows for providing an amide compound with a high yield without generating byproducts such as ammonium sulfate or precipitation of a catalyst-decomposition product, which is industrially suitable.

The Beckmann rearrangement reaction of the present invention does not generate an insoluble matter, so that a reaction solution is not turbid. In other words, no precipitates deposit in a reactor or pipe and thus occlusion or poor heat transfer can be avoided. Since insoluble substances generally having a high boiling point are absent, it is easy to treat a residual tank bottom and a distillation loss is small in purification by distillation of an amide compound produced.

In particular, cyclododecanone-O-azacyclotridecen-2-yloxime or cyclododecanone-O-azacyclotridecen-2-yloxime hydrochloride can be not only a rearrangement catalyst but also a starting material in a Beckmann rearrangement reaction for producing an amide compound, so that processing such as catalyst removal can be eliminated, resulting in easiness to treat and purify. Furthermore, the compound is not hygroscopic nor corrosive, and is stable in the air, and can be, therefore, easily handled.

MODE FOR CARRYING OUT THE INVENTION

An aspect of the present invention relates to a process for producing an amide compound using cyclododecanone-O-azacyclotridecen-2-yloxime, hydrogen chloride and/or a Lewis acid.

Another aspect of the present invention relates to a process for producing an amide compound using cyclododecanone-O-azacyclotridecen-2-yloxime hydrochloride.

In these aspects, cyclododecanone-O-azacyclotridecen-2-yloxime, hydrogen chloride and/or a Lewis acid, or, cyclododecanone-O-azacyclotridecen-2-yloxime hydrochloride can be used as rearrangement catalysts and/or direct starting materials in a Beckmann rearrangement reaction step (whether a batch or continuous process). These will be described in detail.

Cyclododecanone-O-azacyclotridecen-2-yloxime

Cyclododecanone-O-azacyclotridecen-2-yloxime is a novel compound. This compound is a compound represented by Formula (1), a stereoisomer thereof or a mixture of these, which is herein, unless otherwise indicated, described as cyclododecanone-O-azacyclotridecen-2-yloxime.

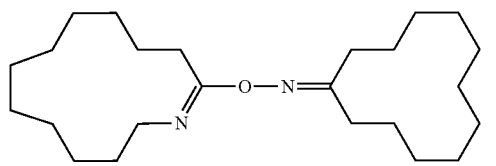

(1)

Cyclododecanone-O-azacyclotridecen-2-yloxime Hydrochloride

Cyclododecanone-O-azacyclotridecen-2-yloxime hydrochloride is a novel compound. This compound is a compound represented by Formula (2), a stereoisomer thereof or a mixture of these, which is herein, unless otherwise indicated, described as cyclododecanone-O-azacyclotridecen-2-yloxime hydrochloride.

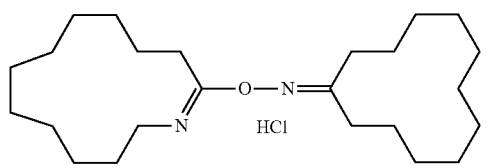 [SMILES: C1CCCCCC(=NO/C2=N/CCCCCCCCCCC2)CCCCC1 ; Cl]

(2)

Process for producing cyclododecanone-O-azacyclotridecen-2-yloxime and cyclododecanone-O-azacyclotridecen-2-yloxime Hydrochloride Cyclododecanone-O-azacyclotridecen-2-yloxime and its hydrochloride can be produced by, for example, the following process. Thionyl chloride is dissolved in a solvent such as anhydrous dichloromethane. To this solution, cyclododecanone oxime in two molar amount to thionyl chloride is added and dissolved and the solvent is evaporated to give cyclododecanone-O-azacyclotridecen-2-yloxime hydrochloride as a white solid. For further purification, it can be purified by column chromatography or recrystallization.

To the cyclododecanone-O-azacyclotridecen-2-yloxime hydrochloride, a solvent is added again and the mixture is washed with an aqueous alkaline solution until an aqueous phase becomes alkaline. Subsequently, an organic phase is collected and the solvent is evaporated to give cyclododecanone-O-azacyclotridecen-2-yloxime after purification such as column chromatography and recrystallization.

Cyclododecanone oxime as a reaction material can be produced from cyclododecanone and hydroxylamine sulfate as described in Patent Document No. 10. A molar ratio of cyclododecanone oxime to thionyl chloride is preferably 2:1 (cyclododecanone oxime thionyl chloride). An excessively larger or smaller molar ratio may lead to increase in impurities other than cyclododecanone-O-azacyclotridecen-2-yloxime, so that subsequent purification becomes complicated. With a smaller molar ratio than the above value, cyclododecanone-O-azacyclotridecen-2-yloxime may be decomposed by unreacted thionyl chloride.

There are no particular restrictions to the above solvent as long as it does not inhibit this reaction, which is preferably aprotic solvent including organohalides such as dichloromethane, aromatic hydrocarbons such as benzene, toluene, xylene, cumene and chlorobenzene, aliphatic hydrocarbons such as n-hexane, n-heptane, n-nonane, cyclohexane, isopropylcyclohexane, cyclooctane, cyclodecane and cyclododecane, ethers such as dioxane and tetrahydrofuran, and mixtures thereof.

A commercially available solvent can be generally used as it is, and is preferably dehydrated before use. A moisture content of the solvent is preferably 1000 ppm or less, more preferably 100 ppm or less. The solvent can be dehydrated by, for example, distillation or adsorptive removal by molecular sieves, preferably distillation.

Cyclododecanone oxime is preferably dissolved to a concentration of 0.1 to 50% by weight, preferably 5 to 50% by weight.

The reaction is preferably conducted under cooling so that a desired product is prevented from being decomposed due to exotherm when thionyl chloride and cyclododecanone oxime is blended, and a reaction temperature is 0 to 60° C., preferably 0 to 40° C.

There are no particular restrictions to a reaction pressure, and the reaction can be conducted at an ambient pressure or under increased pressure.

A reaction time varies depending on reaction conditions such as the above concentration and the temperature, but immediately after blending thionyl chloride and cyclododecanone oxime, cyclododecanone-O-azacyclotridecen-2-yloxime hydrochloride is formed. A reaction time is preferably 60 min or less, and generally a reaction time is within 10 min after dissolution of cyclododecanone oxime. There are no particular restrictions to a reactor, and the reaction can be conducted in a reactor equipped with a common stirrer.

Furthermore, for obtaining cyclododecanone-O-azacyclotridecen-2-yloxime, solid cyclododecanone-O-azacyclotridecen-2-yloxime hydrochloride is re-dissolved in a solvent, and the solution is washed with an aqueous alkaline solution including an aqueous solution containing one or two or more of metal hydroxides such as sodium hydroxide and potassium hydroxide; metal carbonates such as sodium carbonate and potassium carbonate; and metal acetates such as sodium acetate and potassium acetate until the aqueous phase becomes alkaline (pH 7 or more). Here, a solvent used for the re-dissolution can be selected from those used for the above reaction. Although the solvent is not necessarily dehydrated, a moisture content in the solvent is preferably small. Next, the product can be purified by column chromatography or recrystallization to give desired cyclododecanone-O-azacyclotridecen-2-yloxime.

The above cyclododecanone-O-azacyclotridecen-2-yloxime or cyclododecanone-O-azacyclotridecen-2-yloxime hydrochloride can be used as a rearrangement catalyst and/or a reaction starting material in production of an amide compound by a Beckmann rearrangement reaction. When the compound is used as a rearrangement catalyst, an oxime compound is added as a starting material.

Oxime Compound

There are no particular restrictions to an oxime compound in the present invention, and it can be appropriately chosen depending on a desired amide compound. For example, it can be a compound represented by Formula (3).

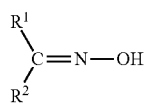

(3)

wherein each $R^1$ and $R^2$ represents an organic group, or $R^1$ and $R^2$ together may represent a divalent organic group, whereby forming a ring with a carbon atom to which $R^1$ and $R^2$ attach.

Examples of the organic group in $R^1$ and $R^2$ include alkyl, alkenyl, alkynyl, cycloalkyl, cycloalkenyl, aryl, aralkyl and aromatic or non-aromatic heterocycle.

The alkyl herein can be, for example, alkyl having 1 to 20 carbon atoms, preferably alkyl having 1 to 12 carbon atoms, more preferably alkyl having 2 to 8 carbon atoms. Specific examples include methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl.

The alkenyl herein can be, for example, alkenyl having 2 to 20 carbon atoms, preferably alkenyl having 2 to 12 carbon atoms, more preferably alkenyl having 2 to 8 carbon atoms. Specific examples include vinyl, allyl, 1-propenyl, 1-butenyl, 1-pentenyl and 1-octenyl.

The alkynyl herein can be, for example, alkynyl having 2 to 20 carbon atoms, preferably alkynyl having 2 to 12 carbon atoms, more preferably alkynyl having 2 to 8 carbon atoms. Specific examples include ethynyl and 1-propynyl.

The cycloalkyl herein can be, for example, cycloalkyl having 3 to 20 carbon atoms, preferably cycloalkyl having 3 to 15 carbon atoms. Specific examples include cyclopropyl, cyclobutyl, cyclopentyl, cyclohexyl, cycloheptyl, cyclooctyl and cyclododecyl.

The cycloalkenyl herein can be, for example, cycloalkenyl having 3 to 20 carbon atoms, preferably cycloalkenyl having 3 to 15 carbon atoms. Specific examples include cyclopentenyl, cyclohexenyl and cyclooctenyl.

Examples of the aryl include phenyl and naphthyl.

Examples of the aralkyl include benzyl, 2-phenylethyl and 3-phenylpropyl.

Examples of the aromatic or non-aromatic heterocycle include 2-pyridyl, 2-quinolyl, 2-furyl, 2-thienyl and 4-piperidinyl.

When $R^1$ and $R^2$ together represent a bivalent organic group, they form a ring with the carbon atom to which they attach, and the bivalent organic group is straight or branched-chain alkylene, preferably straight alkylene, and the ring formed is, for example, a 3- to 30-membered ring, preferably a 4- to 20-membered ring, further preferably a 5- to 14-membered ring.

Such an organic group, whether it forms a ring or not, can be substituted by any of various substituents as long as the reaction is not inhibited. Examples of such a substituent include halogen, oxo, mercapto, substituted oxy (alkoxy, acyloxy, acylloxy and so on), substituted thio, substituted oxycarbonyl, substituted or unsubstituted carbamoyl, cyano, nitro, substituted aminoalkyl, alkenyl, alkynyl, cycloalkyl, cycloalkenyl, aryl (phenyl, naphthyl and so on), aralkyl and heterocycle.

Specific examples of an oxime compound represented by Formula (3) include acetone oxime, 2-butanone oxime, 2-pentanone oxime, 3-pentanone oxime, 1-cyclohexyl-1-propanone oxime, benzaldehyde oxime, acetophenone oxime, benzophenone oxime and 4-hydroxyacetophenone oxime and examples of a ring-forming oxime include cyclopropanone oxime, cyclobutanone oxime, cyclopentanone oxime, cyclohexanone oxime, cycloheptanone oxime, cyclooctanone oxime, cyclononanone oxime, cyclodecanone oxime, cyclododecanone oxime, cyclotridecanone oxime, cyclotetradecanone oxime, cyclopentadecanone oxime, cyclohexadecanone oxime, cyclooctadecanone oxime and cyclononadecanone oxime.

One or two or more oxime compounds can be selected to be used.

An oxime compound can be prepared by reacting a ketone corresponding to an oxime compound represented by Formula (3) with hydroxylamine. For example, cyclododecanone oxime can be prepared by reacting cyclododecanone with hydroxylamine generated by double decomposition of hydroxylamine sulfate as described in Japanese Laid-open Patent Publication No. 2004-59553.

It can be also prepared by reacting a methyl- or methylene-containing compound with an ester or salt of nitrous acid in the presence of an N-hydroxyamide compound derived from an aliphatic polycarboxylic anhydride (cyclic anhydride) or aromatic polycarboxylic anhydride (cyclic anhydride) such as N-hydroxysuccinimide, N-hydroxyphthalimide, N,N'-dihydroxypyromellitic diimide, N-hydroxyglutarimide, N-hydroxy-1,8-naphthalenedicarboxylic imide and N,N'-dihydroxy-1,8,4,5-naphthalenetetracarboxylic diimide and a compound prepared by introducing a protecting group (for example, acyl such as acetyl) into hydroxyl in the N-hydroxyamide compound (for example, see Japanese published unexamined application No. 2009-298706).

Alternatively, it can be produced, for example, by photo-nitrosation of a cycloalkane or a reaction of a cycloalkanone with ammonia and hydrogen peroxide in the presence of a catalyst such as titanium silicate.

Next, as one aspect of the present invention, there will be described a process for producing laurolactam using cyclododecanone-O-azacyclotridecen-2-yloxime.

Process for Producing Laurolactam Using cyclododecanone-O-azacyclotridecen-2-yloxime Cyclododecanone-O-azacyclotridecen-2-yloxime can be used as a catalyst for Beckmann rearrangement in combination with hydrogen chloride and/or a Lewis acid in producing laurolactam from cyclododecanone oxime. Alternatively, it can be used as a direct reaction starting material in producing laurolactam. In the present invention, a rearrangement reaction liquid contains, except laurolactam, only hydrogen chloride and/or a Lewis acid, which can be advantageously removed by convenient neutralization.

When cyclododecanone-O-azacyclotridecen-2-yloxime to which hydrogen chloride and/or a Lewis acid are added is used as a Beckmann rearrangement catalysts in a rearrangement reaction, cyclododecanone-O-azacyclotridecen-2-yloxime is used in an amount of 50 mol % or less, preferably 20 mol % or less, more preferably 10 mol % or less, and generally 0.1 mol % or more (when an Lewis acid or a combination of hydrogen chloride and a Lewis acid is used, it is preferably 0.5 mol % or more. while when hydrogen chloride is used in the absence of a Lewis acid, it is preferably 1 mol % or more, more preferably 2 mol % or more) to cyclododecanone oxime. Since cyclododecanone-O-azacyclotridecen-2-yloxime also gives laurolactam, pure laurolactam can be provided.

When hydrogen chloride (HCl) is added to cyclododecanone-O-azacyclotridecen-2-yloxime, the amount of hydrogen chloride (HCl) is equal molar or more, preferably 1 to 10 molar, more preferably 1 to 5 molar to cyclododecanone-O-azacyclotridecen-2-yloxime.

When a Lewis acid is added to cyclododecanone-O-azacyclotridecen-2-yloxime (when hydrogen chloride is absent), the Lewis acid is preferably halides of one or two or more metals selected from the group consisting of tin and bismuth; specifically, tin tetrafluoride, tin tetrachloride, tin tetrabromide, bismuth trifluoride, bismuth trichloride and bismuth tribromide.

When cyclododecanone-O-azacyclotridecen-2-yloxime is mixed with a Lewis acid, the amount of the Lewis acid is 0.01 to 10 molar, preferably 0.1 to 5 molar to cyclododecanone-O-azacyclotridecen-2-yloxime. If the amount of the Lewis acid is too small, it is less effective in improving a rearrangement rate while an excessive amount does not contribute further improvement in a rearrangement rate and leads to increase in a cost for post-processing or recycling a Lewis acid, which is industrially undesirable.

By adding a Lewis acid in combination with hydrogen chloride, cyclododecanone-O-azacyclotridecen-2-yloxime can express or increase its rearrangement activity in producing laurolactam from cyclododecanone oxime. The Lewis acid is preferably halides of one or two or more metals selected from the group consisting of zinc, cobalt, antimony, tin and bismuth; specific examples include zinc fluoride, zinc chloride, zinc bromide, cobalt fluoride, cobalt chloride, cobalt bromide, antimony pentafluoride, antimony pentachloride, antimony pentabromide, tin tetrafluoride, tin tetrachloride, tin tetrabromide, bismuth trifluoride, bismuth trichloride and bismuth tribromide. The amounts of hydrogen chloride (HCl) and Lewis acid are as described above.

There are no particular restrictions to a method for adding hydrogen chloride and/or a Lewis acid, and they can be added to a solution of cyclododecanone oxime together with cyclododecanone-O-azacyclotridecen-2-yloxime and the mixture can be then introduced in a reactor. Alternatively, a predetermined amount of cyclododecanone-O-azacyclotridecen-2-yloxime and a predetermined amount of hydrogen chloride (HCl) and/or a Lewis acid can be previously dissolved in a solvent used for a Beckmann rearrangement reaction, and then, the mixture can be introduced to a reactor charged with a solution of cyclododecanone oxime. Alternatively, a solution of a predetermined amount of hydrogen chloride and/or a Lewis acid in a solvent used for the reaction can be fed into a reactor charged with a solution of cyclododecanone oxime and a reactor charged with a solution of cyclododecanone-O-azacyclotridecen-2-yloxime, respectively.

In general, such a rearrangement reaction of cyclododecanone oxime is conducted preferably in a solvent, which can be any solvent as long as it does not inhibit the reaction; for example, aromatic hydrocarbons such as benzene, toluene, xylene, cumene and chlorobenzene; aliphatic hydrocarbons such as n-hexane, n-heptane, n-nonane, cyclohexane, isopropylcyclohexane, cyclooctane, cyclodecane and cyclododecane; ketone compounds such as acetone, methyl ethyl ketone, methyl isopropyl ketone, methyl isobutyl ketone, cyclohexanone and cyclododecanone; nitriles such as acetonitrile, propionitrile and benzonitrile; amides such as N,N-dimethylformamide, N,N-dimethylacetamide, N-methylpyrrolidone and 1,3-dimethyl-2-imidazolinone; sulfoxides and sulfones such as dimethyl sulfoxide and sulfolane; esters such as ethyl formate, methyl acetate, ethyl acetate, methyl propionate and ethyl butanoate; ethers such as diethyl ether, diisopropyl ether, tetrahydrofuran and dioxane; and mixtures thereof. It is preferably selected from aromatic hydrocarbons and nitriles, particularly preferably toluene and acetonitrile. The solvent can be dehydrated or a commercial product as it is without an especial dehydration treatment.

The amount of the solvent is, but not limited to, generally 0.3 to 100 parts by weight, preferably 1 to 50 parts by weight to one part of cyclododecanone oxime.

A reaction temperature is preferably, but not limited to, in the range of 0 to 150° C.

The atmosphere of the reaction can be any gas inert to the reaction; preferably an inert atmosphere such as nitrogen and argon.

There are no particular restrictions to a reaction pressure, and the reaction can be under an ambient pressure or under increased pressure.

A reaction time varies depending on the reaction conditions such as the above concentrations and the temperature, and can be generally 0.01 to 24 hours, preferably, 0.05 to 10 hours.

There are no particular restrictions to a reactor, and any reactor equipped with a common stirrer can be used.

As process after the reaction, the reaction can be neutralized with an alkaline solution such as an aqueous solution containing one or two or more metal hydroxides such as sodium hydroxide and potassium hydroxide; metal carbonates such as sodium carbonate and potassium carbonate; and metal acetates such as sodium acetate and potassium acetate and then washed with water, and the resulting solution can be evaporated to provide laurolactam. Laurolactam obtained in the present invention can be further separated and purified by a common procedure such as distillation and crystallization.

There are no particular restrictions to a device and a reactor equipped with a common stirrer can be used.

Alternatively, cyclododecanone-O-azacyclotridecen-2-yloxime is blended with hydrogen chloride and/or Lewis acid in the absence of cyclododecanone oxime, and the mixture can be used as a direct reaction starting material for a Beckmann rearrangement reaction to give laurolactam. Here, hydrogen chloride and/or a Lewis acid, a solvent, their amounts, the reaction conditions and so forth can be as described for the method using cyclododecanone-O-azacyclotridecen-2-yloxime as a catalyst.

As another aspect of the present invention, there will be described a process for producing laurolactam using cyclododecanone-O-azacyclotridecen-2-yloxime hydrochloride.

Process for Producing Laurolactam Using cyclododecanone-O-azacyclotridecen-2-yloxime Hydrochloride Cyclododecanone-O-azacyclotridecen-2-yloxime hydrochloride can be used as a Beckmann rearrangement catalyst in producing laurolactam from cyclododecanone oxime. Furthermore, a Lewis acid can be added as a co-catalyst to increase catalyst activity, so that even a small amount of cyclododecanone-O-azacyclotridecen-2-yloxime hydrochloride can be effective in producing a corresponding laurolactam from cyclododecanone oxime.

Cyclododecanone-O-azacyclotridecen-2-yloxime hydrochloride can be used as a solution as prepared by mixing cyclododecanone oxime and thionyl chloride in a solvent or as a solid after evaporating the solvent.

When cyclododecanone-O-azacyclotridecen-2-yloxime hydrochloride is used as a catalyst in the rearrangement reaction, the amount of cyclododecanone-O-azacyclotridecen-2-yloxime hydrochloride is as in the use of cyclododecanone-O-azacyclotridecen-2-yloxime. Since cyclododecanone-O-azacyclotridecen-2-yloxime hydrochloride also gives laurolactam, pure laurolactam can be obtained. A rearrangement reaction liquid contains, except laurolactam, only a Lewis acid and hydrogen chloride, which can be removed by convenient neutralization.

A mixture of cyclododecanone-O-azacyclotridecen-2-yloxime hydrochloride with a Lewis acid can be used in the rearrangement reaction. Examples of a Lewis acid is preferably halides of one or two or more metals selected from the group consisting of zinc, cobalt, antimony, tin and bismuth; specific examples include zinc fluoride, zinc chloride, zinc bromide, cobalt fluoride, cobalt chloride, cobalt bromide, antimony trifluoride, antimony pentafluoride, antimony trichloride, antimony pentachloride, antimony tribromide, antimony pentabromide, tin tetrafluoride, tin tetrachloride (stannic chloride), tin tetrabromide, bismuth trifluoride, bismuth trichloride and bismuth tribromide.

The amount of the Lewis acid is 0.01 to 10 molar, preferably 0.1 to 5 molar to cyclododecanone-O-azacyclotridecen-2-yloxime hydrochloride. If the amount of the Lewis acid is too small, it is less effective in improving a rearrangement rate while an excessive amount does not contribute further improvement in a rearrangement rate and leads to increase in a cost for post-processing or recycling a Lewis acid, which is industrially undesirable.

As a method for adding Lewis acid, it can be added to a solution of cyclododecanone oxime together with cyclododecanone-O-azacyclotridecen-2-yloxime hydrochloride, and then, the mixture can be fed into a reactor. Alternatively, a predetermined amount of cyclododecanone-O-azacyclotridecen-2-yloxime hydrochloride and a predetermined amount of a Lewis acid can be previously dissolved in a solvent used for the reaction, and then, the mixture is fed to a reactor charged with a solution of cyclododecanone oxime. Alternatively, a solution of a predetermined amount of a Lewis acid in a solvent used for the reaction can be fed into a reactor charged with a solution of cyclododecanone oxime and a reactor charged with a solution of cyclododecanone-O-azacyclotridecen-2-yloxime hydrochloride, respectively.

When cyclododecanone-O-azacyclotridecen-2-yloxime hydrochloride is used in a Beckmann rearrangement reaction, a solvent, the amount of the solvent, a reaction temperature, a reaction atmosphere, a reaction pressure, a reaction time, a reaction apparatus and process after the rearrangement reaction are as described in the Beckmann rearrangement reaction using cyclododecanone-O-azacyclotridecen-2-yloxime.

Alternatively, a Beckmann rearrangement reaction can be conducted for producing laurolactam using cyclododecanone-O-azacyclotridecen-2-yloxime hydrochloride as a direct reaction starting material in the absence of cyclododecanone oxime. Here, cyclododecanone-O-azacyclotridecen-2-yloxime hydrochloride is dissolved in a solvent and then heated. Alternatively, without using cyclododecanone oxime, cyclododecanone-O-azacyclotridecen-2-yloxime hydrochloride is used as a direct reaction starting material together with a Lewis acid as a co-catalyst in a reaction step, to conduct a Beckmann rearrangement reaction. Here, a Lewis acid, the reaction conditions and so on are as described for the case using cyclododecanone-O-azacyclotridecen-2-yloxime hydrochloride as a rearrangement catalyst.

Process for Producing an Amide Compound Having a Pre-Preparation Step

Another aspect of the present invention provides a process for producing an amide compound by Beckmann rearrangement of an oxime compound using thionyl chloride as a rearrangement catalyst, having the steps of pre-preparation (described later) and a rearrangement reaction. In the pre-preparation step, a chlorine-containing catalytically active species (intermediate) is formed, and in the rearrangement reaction step, Beckmann rearrangement reaction is conducted using the catalytically active species. The inventors of the present invention have found that when cyclododecanone oxime is used as one of oxime compounds, a catalytically active species in a reaction liquid obtained by the pre-preparation step is the above cyclododecanone-O-azacyclotridecen-2-yloxime hydrochloride, which gives cyclododecanone-O-azacyclotridecen-2-yloxime by treatment with an alkali. These will be detailed below.

There will be detailed a mechanism of a reaction forming the above catalytically active species in the pre-preparation step. First, hydrogen chloride is eliminated from thionyl chloride and the oxime compound to form a compound having a structure represented by Formula (4), and then an intramolecular nucleophilic substitution reaction of the compound of Formula (4) occurs to give a compound represented by Formula (5). Here, the sulfur atom is eliminated as sulfur dioxide.

It is suggested by the following results. A solution containing a pre-prepared catalytically active species (hereinafter, referred to as a "pre-preparation solution") was degassed under a reduced pressure to remove a gas generated by elimination and the residual thionyl chloride. The sample was combusted by an automatic sample combustion apparatus (for example, type AQF-100 from Mitsubishi Chemical Corporation) and a gas generated was absorbed by an aqueous alkaline solution, which was then analyzed by ion chromatography (for example, ICS1000 system from DIONEX). Chlorine was detected in an about 0.5-fold amount of the thionyl chloride fed and a trace amount of sulfur was detected.

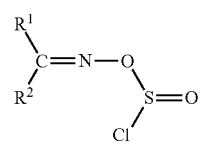

(4)

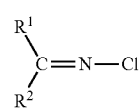

(5)

Here, bonding electrons are localized to Cl and the nitrogen atom is electron-poor while Beckmann rearrangement proceeds and an amide or lactam intermediate represented by Formula (6) or (6') is formed.

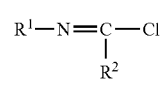

(6)

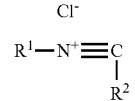

(6')

The amide or lactam intermediate represented by Formula (6) or (6') reacts with an oxime compound to give a chlorine-containing oxime-amide (or oxime-lactam) intermediate represented by Formula (7)

(7)

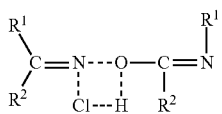

An amide (or lactam) is eliminated from the oxime-amide (or oxime-lactam) intermediate (Formula (7)) to regenerate the compound represented by Formula (5), and thus a catalyst cycle is completed.

When the oxime compound represented by Formula (3) is cyclododecanone oxime, the intermediate represented by Formula (7) can be isolated. An alkali was added for removing hydrogen chloride (HCl) to stabilize the product, which was then recrystallized. Then, it was confirmed that the analysis of X-ray diffraction demonstrated that the product is the above cyclododecanone-O-azacyclotridecen-2-yloxime represented by the Formula (1).

A catalytic amount of the isolated intermediate was used in a Beckmann rearrangement reaction of cyclododecanone oxime whereby the reaction quickly proceeds to give laurolactam in a high yield. These results show that the isolated intermediate is the above cyclododecanone-O-azacyclotridecen-2-yloxime hydrochloride represented by Formula (2).

Furthermore, a compound represented by Formula (8) which is produced by rearrangement of the oxime moiety in the intermediate (Formula (7)) would be also a catalytically active species. Namely, a cycle in which an amide (or lactam) moiety is eliminated from the compound represented by Formula (8) to regenerate the amide or lactam intermediate represented by Formula (6) or Formula (6') would be also speculated.

In other words, the catalyst cycle in this rearrangement reaction is represented by catalyst cycle (1) or (2) (the numbers in parenthesis in the schemes indicate corresponding compound numbers. For example, (5) indicates the compound represented by Formula (5)). In any reaction path, a stable intermediate is the compound represented by Formula (7) (catalytically active species).

Meanwhile, the intermediate (Formula (7) (catalytically active species)) itself is sometimes decomposed into an amide (or lactam) and an oxime. In this case, the catalyst cycle represented catalyst cycle (1) or (2) is broken, resulting in decrease of turnover of a catalyst. Therefore, in the pre-preparation, the conditions must be selected so that the chlorine-containing intermediate (Formula (7)) as a catalytically active species can be obtained in a high yield.

Furthermore, it is preferable to avoid generation and co-existence of the amide (or lactam) in the pre-preparation for preventing reversal of the catalyst cycle.

(8)

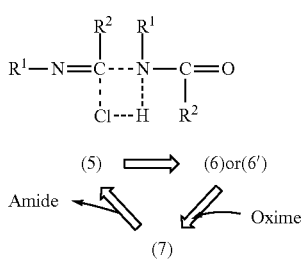

Catalyst cycle(1)

-continued

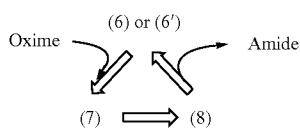

Catalyst cycle (2)

There will be described a preferable aspect in the step of pre-preparation.

Apparatus for the Pre-Preparation

An apparatus used for the pre-preparation preferably consists of three units, that is, a mixing unit, a pipe for a mixed liquid and a degassing tank.

As the mixing unit, a unit simply mixing thionyl chloride and an oxime compound in pipes; a line mixer improving blending of thionyl chloride and an oxime compound, or a unit equipped with a stirrer can be used. When the reaction is stirred, its residence time in the mixing unit is preferably short, generally 5 min or less, preferably 2 min or less. With an excessively long residence time, an amide or lactam compound generated by decomposition of a catalytically active species (Formula (7)) (when cyclododecanone oxime is used as a starting material, the compound represented by Formula (2)) inhibits generation of (7) from (6) or (6') and generation of an oxime compound as described above, and therefore, a yield of the catalytically active species (Formula (7)) in the pre-preparation is reduced. Furthermore, such a reaction apparatus can be equipped with a cooling means such as a jacket for allowing a mixing unit temperature to be lowered.

A pipe for a mixed liquid is a tube with a diameter ensuring plug flowability and can be equipped with a cooling means such as a jacket.

A degassing tank is a tank having a gas section. The degassing tank preferably has a configuration in which an inert gas such as nitrogen can be bubbled into a liquid to actively expel a generated gas. Furthermore, the degassing tank can be equipped with a cooling means such as a jacket.

Time for Degassing in the Pre-Preparation

In the pre-preparation, a time from mixing thionyl chloride and an oxime compound to degassing the mixture in a degassing tank varies depending on a temperature of a mixing unit. For example, the time is preferably 40 min or less and 60 min or less at 60° C. and 40° C., respectively.

A time over the above residence time is undesirable because catalyst activity is deteriorated in a Beckmann rearrangement reaction due to decomposition of a catalytically active species (Formula (7), and when cyclododecanone oxime is used as a staring material, the compound of Formula (2)). Furthermore, an excessively longer residence time is industrially undesirable due to the necessity for a larger apparatus.

Mixing Ratio in the Pre-Preparation

In the pre-preparation step, the whole or a partial amount of an oxime compound to be involved in a rearrangement reaction can be used. A mixing ratio of thionyl chloride to an oxime compound in the pre-preparation (a molar ratio of an oxime compound/thionyl chloride) is 2.0 or more and 10.0 or less, preferably 2.0 or more and 5.0 or less, further preferably 2.0 or more and 3.0 or less.

Thionyl chloride is used in an amount of preferably 0.01 mol % to 20 mol %, more preferably 0.1 mol % to 5 mol % to the whole amount of the oxime compound used in the pre-preparation and the rearrangement reaction steps.

A too small amount of thionyl chloride is undesirable because the rearrangement reaction does not proceed. On the other hand, an excessively large amount of thionyl chloride is industrially undesirable due to increase in a catalyst cost and a cost for post-processing the catalyst.

If the mixing ratio in the pre-preparation is too small, a major part of thionyl chloride does not involve in forming a catalytically active species, leading to inefficient pre-preparation.

A too large mixing ratio in the pre-preparation is undesirable due to the necessity for a larger pre-preparation apparatus. For example, when cyclododecanone oxime is used as an oxime compound, cyclododecanone oxime and a catalytically active species generated in the pre-preparation are poorly soluble in a solvent described later at a temperature described later, and therefore, a large amount of solvent is required for preventing precipitation of a solid or clogging in the pre-preparation step, disadvantageously resulting in the necessity for a large pre-preparation apparatus. Furthermore, an energy cost for collection and recycling of a solvent is disadvantageously increased.

Temperature in the Pre-Preparation

A temperature of the mixing unit and the degassing tank in the pre-preparation is a temperature or lower of a Beckmann rearrangement reaction, preferably 100° C. or less, more preferably 60° C. or less. An excessively higher temperature in the pre-preparation is undesirable because most of a catalytically active species is converted to an amide or lactam compound, leading to deterioration in catalyst activity. There are no particular restrictions to a lower limit of a preparation temperature as long as the reaction system is not solidified at the temperature, but a temperature of 10° C. or lower, furthermore 0° C. or lower requires a cooling means, which is uneconomical. For example, when the oxime compound is cyclododecanone oxime, a temperature of the mixing unit and the degassing tank in the pre-preparation is preferably 60° C. or less. Since industrially a reaction system involving no precipitants is easily handled, a temperature is preferably 25° C. or more for preventing a catalytically active species (the compound of Formula (2)) from precipitating when the solvent is toluene.

Solvent for the Pre-Preparation

Suitable solvents used in the pre-preparation are as follows.

There are no particular restrictions to a solvent used in the present invention as long as it is inert to a rearrangement catalyst or an oxime compound. Examples of a solvent which can be used include nitriles such as acetonitrile, propionitrile and benzonitrile; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; and mixtures thereof. Among these, aliphatic hydrocarbons and aromatic hydrocarbons are particularly suitable solvents because a rate of the Beckmann rearrangement reaction in the pre-preparation can be easily controlled.

Unsuitable solvents are those having an active hydroxyl group or a similar functional group such as organic bases including amines, water, alcohols and mercaptanes, and those reactive to thionyl chloride as a chlorinating agent such as carboxylic acids and carboxylic acid esters.

The above solvents can be also used when a Lewis acid is used as a co-catalyst in a rearrangement reaction.

While an amount of a solvent in the pre-preparation is determined depending on, but not limited to, a temperature, the size of a mixing unit, a degassing tank or the like, when an oxime compound is cyclododecanone oxime and a solvent is toluene, a weight concentration of cyclododecanone oxime is preferably 1% or more and 60% or less, particularly preferably 3% or more and 30% or less. A too small amount of toluene is undesirable because cyclododecanone oxime and an intermediate generated cannot be adequately dissolved, while a too large amount of toluene is undesirable because recovery becomes troublesome and thus uneconomical.

The conditions of the pre-preparation beyond the above ranges are undesirable because a molar production ratio of a catalytically active species (Formula (7)) in a pre-preparation solution to thionyl chloride added in the pre-preparation is reduced and at the same time, an oxime conversion in the rearrangement reaction is reduced. A molar production ratio of a catalytically active species (Formula (7)) in a pre-preparation solution to thionyl chloride is 50% or more, preferably 80% or more, further preferably 90% or more when the oxime compound is cyclododecanone oxime. A conversion in the rearrangement reaction is 98% or more, preferably 99% or more, and when laurolactam is purified by distillation, the conversion is further preferably 99.5% or more for size reduction of a distillation apparatus.

There will be described aspects of a rearrangement reaction. Here, a solution containing a catalytically active species pre-prepared is introduced into a Beckmann rearrangement reaction tank, and reacts with an oxime compound separately fed into the reaction tank, to generate an amide or lactam compound.

Beckmann Rearrangement Reaction

When only a part of an oxime compound is used in the pre-preparation, the pre-preparation solution and an additional part of the oxime compound are mixed in a Beckmann rearrangement reaction.

Co-Catalyst

In a Beckmann rearrangement reaction, acids such as hydrogen chloride can be added as a co-catalyst to improve a rate of the rearrangement reaction. In particular, a Lewis acid is preferable because it can improve a rate of the rearrangement reaction without accelerating hydrolysis of an oxime compound such as cyclododecanone oxime.

The Lewis acid is a halide of one or two or more metals selected from the group consisting of zinc, cobalt, antimony, tin and bismuth; specifically zinc fluoride, zinc chloride, zinc bromide, cobalt fluoride, cobalt chloride, cobalt bromide, antimony pentafluoride, antimony pentachloride, antimony pentabromide, tin tetrafluoride, tin tetrachloride, tin tetrabromide, bismuth trifluoride, bismuth trichloride and bismuth tribromide. Among these, zinc chloride and tin tetrachloride are suitable and zinc chloride is particularly preferable because an effect in improvement of a reaction rate is significant.

The amount of a co-catalyst is 0.01 to 10 molar, preferably 0.1 to 5 molar to thionyl chloride. A too small amount of a Lewis acid is less effective in improving a rate of the rearrangement reaction while an excessive amount does not contribute further improvement in a rearrangement rate and leads to increase in a cost for post-processing and recycling the co-catalyst, which is industrially undesirable.

Solvent Used for a Beckmann Rearrangement Reaction

Although preferably a solvent used in a Beckmann rearrangement reaction is identical to the solvent used in the pre-preparation in the light of simplifying a production process, a different solvent can be used. When a different solvent is used, for example, solvent exchange to a rearrangement solvent can be conducted by adding a rearrangement solvent to a pre-preparation solution and then evaporating a pre-preparation solvent. Alternatively, a Beckmann rearrangement reaction can be conducted in a mixture of the pre-preparation solvent and the rearrangement solvent.

Temperature of a Beckmann Rearrangement Reaction

A temperature of a Beckmann rearrangement reaction is 60° C. to 160° C., preferably 80° C. to 150° C. A too low reaction temperature is undesirable because a reaction rate becomes so small for the reaction to stop. Furthermore, at a low temperature, solidification of an oxime compound or its poor solubility in a rearrangement solvent may cause its precipitation, leading to problems in operation. Increasing the amount of a solvent in order to avoid the problems is not preferable because it causes problems such that a production cost is increased due to increase of recovering and recycling the solvent. A too high reaction temperature is also undesirable because the rearrangement reaction becomes so exothermic that a temperature rapidly rises and thus the reaction cannot be controlled. Furthermore, at a too high reaction temperature, a rearrangement yield is reduced due to side reactions such as a condensation reaction and product quality is deteriorated due to staining and so on. For example, when the oxime compound is cyclododecanone oxime, a temperature of a Beckmann rearrangement reaction is preferably 80 to 130° C.

Reaction Time of Beckmann Rearrangement Reaction

While a reaction time of Beckmann rearrangement varies depending on various factors such as concentrations of an oxime compound and thionyl chloride and a reaction temperature, it is generally 5 min to 10 hours, preferably 10 min to 4 hours.

These reaction conditions of Beckmann rearrangement are determined such that the reaction can be easily controlled and the reaction does not require an extraordinarily large reactor volume.

Pressure of a Beckmann Rearrangement Reaction

A Beckmann rearrangement reaction can be conducted under a reduced pressure, ambient pressure or increased pressure.

Apparatus Used in a Beckmann Rearrangement Reaction

A continuous flow device used in a Beckmann rearrangement reaction can be a generally used reactor such as a tubular continuous reactor and a stirring tank type continuous reactor, but a multistage continuous tank type reactor is suitable because of easier reaction temperature control and simple operation.

Separation and Purification of Reaction Products of Beckmann Rearrangement

At the end of a Beckmann rearrangement reaction, a product can be separated and purified by a separation procedure such as filtration, concentration, distillation, extraction, crystallization, recrystallization, absorption and column chromatography and combination thereof.

For example, in terms of treatment of cyclododecanone oxime after the reaction, water is added to a reaction mixture of the Beckmann rearrangement reaction, and the resulting mixture is extracted with an organic solvent and the solvent can be evaporated to give laurolactam, which can be further separated and purified by distillation, crystallization and the like.

EXAMPLES

The present invention will be further detailed with reference to, but not limited to, Examples.

Example A1

Process for Producing Cyclododecanone-O-azacyclotridecen-2-yloxime

In 20 g of dichloromethane, 0.618 g (5.19 mmol) of thionyl chloride was dissolved. Under ice-cooling, 2.05 g (10.39 mmol) of cyclododecanone oxime was added to the solution and dissolved. Immediately after dissolution, dichloromethane was removed from this solution by an evaporator to give a white powder. The white powder was dissolved in dichloromethane. The solution was transferred in a separatory funnel and washed three times with 20 mL of 0.5 N NaOH (a 0.5 N aqueous solution of sodium hydroxide) until an aqueous layer became alkaline as determined by a pH test paper. Then, the dichloromethane solution was washed three times with pure water and then dried over anhydrous magnesium sulfate. Anhydrous magnesium sulfate was removed by filtration from the dichloromethane solution and dichloromethane was evaporated to give 1.89 g of a white powder (yield: 96.4%). The white powder was recrystallized from a mixture of dichloromethane/acetone (mixed solvent: dichloromethane/acetone=1/4 (by weight), recrystallization temperature: −10 to −15° C.), to give cyclododecanone-O-azacyclotridecen-2-yloxime as colorless crystals (melting point: 85.4 to 87.3° C.).

The product was identified by elementary analysis, $^1$H-NMR, $^{13}$C-NMR and MS. The results supported the structure of cyclododecanone-O-azacyclotridecen-2-yloxime. This compound is novel.

(1) Elementary Analysis
Observed (%) H, 11.48; C, 75.73, N, 7.29
Calculated (%) H, 11.78; C, 76.54, N, 7.44.
(as $C_{24}H_{44}N_2O$)
(2) $^1$H-NMR (500 MHz, $CDCl_3$ solvent)
1.30-1.75 (36H, m), 2.32-2.35 (2H, m), 2.44-2.47 (2H, m), 2.58-2.60 (2H, m), 3.35-3.37 (2H, m).
(3) $^{13}$C-NMR (125 MHz, $CDCl_3$ solvent)
22.53, 23.02, 23.33, 23, 43, 23.67, 24.01, 24.61, 24.69, 25.07, 25.16, 25.32, 25.69, 25.81, 25.86, 25.90, 26.64, 26.86, 28.31, 29.35, 30.35, 32.24, 44.91, 160.84, 162.82.
(4) MS spectrum
EI-MS m/z 376 (M), CI-MS m/z 377 (MH).

Example A2

Into a glass reaction tube (volume: 30 mL), 1.0 g of cyclododecanone oxime (Tokyo Chemical Industry Co., Ltd.) was charged under an ambient atmosphere, and then 3.7 g of toluene (Wako Pure Chemical Industries, Ltd.) as a solvent was added in a glove box under a nitrogen gas atmosphere, and then the tube was sealed and taken out from the glove box. Separately, in a glove box, 0.804 g of a dioxane solution containing 1.48% by weight of dry HCl (HCl content: 0.325 mmol) and 0.498 g of dichloromethane were added to 0.0605 g of cyclododecanone-O-azacyclotridecen-2-yloxime (0.161 mmol) to prepare a solution (a molar ratio of cyclododecanone-O-azacyclotridecen-2-yloxime to HCl=1.0/2.0), and the vessel was sealed and taken out from the glove box. The above reaction tube containing cyclododecanone oxime was placed in an oil bath at 105° C., and after an internal temperature reached 100° C., 1.264 g of the above solution of cyclododecanone-O-azacyclotridecen-2-yloxime (0.150 mmol of cyclododecanone-O-azacyclotridecen-2-yloxime (3 mol % of cyclododecanone oxime) and 0.320 mmol of HCl (6 mol % of cyclododecanone oxime)) were injected into the reaction tube by a syringe. After one hour, the reaction tube was taken out from the oil bath and allowed to be cooled.

After the reaction solution was diluted with toluene, products were quantitatively analyzed by high performance liquid chromatography. The results are shown in Table 1.

The analysis conditions of the high performance liquid chromatography were as follows.

Column: J'sphere ODS-H80, column temperature: 40° C., eluant: acetonitrile/water (volume ratio: 55/45), flow rate: 1 mL/min, detection wavelength: 210 nm.

A yield of laurolactam was determined according to the following equation.

Yield of laurolactam (%)=100×(mol number of laurolactam produced)/{(mol number of cyclododecanone oxime)+2×(mol number of cyclododecanone-O-azacyclotridecen-2-yloxime)}

Example A3

A procedure was conducted as described for Example A2, except that the amounts of cyclododecanone-O-azacyclotridecen-2-yloxime and HCl were 3.00 mol % and 9.77 mol % to cyclododecanone oxime, respectively.

After the reaction solution was diluted with toluene, products were quantitatively analyzed by high performance liquid chromatography. The results are shown in Table 1.

Example A4

A procedure was conducted as described for Example A2, except that the amounts of cyclododecanone-O-azacyclotridecen-2-yloxime and HCl were 4.08 mol % and 8.08 mol % to cyclododecanone oxime, respectively.

After the reaction solution was diluted with toluene, products were quantitatively analyzed by high performance liquid chromatography. The results are shown in Table 1.

Example A5

A procedure was conducted as described for Example A2, except that the amounts of cyclododecanone-O-azacyclotridecen-2-yloxime and HCl were 5.20 mol % and 5.56 mol % to cyclododecanone oxime, respectively.

After the reaction solution was diluted with toluene, products were quantitatively analyzed by high performance liquid chromatography. The results are shown in Table 1.

Example A6

A procedure was conducted as described for Example A2, except that the amounts of cyclododecanone-O-azacyclotridecen-2-yloxime and HCl were 4.67 mol % and 7.15 mol % to cyclododecanone oxime, respectively.

After the reaction solution was diluted with toluene, products were quantitatively analyzed by high performance liquid chromatography. The results are shown in Table 1.

Example A7

A procedure was conducted as described for Example A2, except that the amounts of cyclododecanone-O-azacyclotridecen-2-yloxime and HCl were 5.24 mol % and 10.38 mol % to cyclododecanone oxime, respectively.

After the reaction solution was diluted with toluene, products were quantitatively analyzed by high performance liquid chromatography. The results are shown in Table 1.

Comparative Example A1

A procedure was conducted as described for Example A2, except that 0.0954 g of cyclododecanone-O-azacyclotridecen-2-yloxime (0.254 mmol, 5.00 mol % of cyclododecanone oxime) was added and HCl was absent.

After the reaction solution was diluted with toluene, products were quantitatively analyzed by high performance liquid chromatography. The results are shown in Table 1.

Comparative Example A2

A procedure was conducted as described for Example A2, except that cyclododecanone-O-azacyclotridecen-2-yloxime was absent and only 0.640 g of a dioxane solution containing 1.48% by weight of dry HCl (HCl content: 0.256 mmol, 5.01 mol % of cyclododecanone oxime) was added.

After the reaction solution was diluted with toluene, products were quantitatively analyzed by high performance liquid chromatography. The results are shown in Table 1.

TABLE 1

| | Cyclododeca-none-O-aza-cyclotridecen-2-yloxime (mol %) | Hydrogen chloride (HCl)/cyclo-dodecanone oxime (mol %) | Reaction results | |
|---|---|---|---|---|
| | | | Conversion of cyclodo-decanone oxime (%) | Yield of lauro-lactam (%) |
| Example A2 | 3.00 | 6.00 | 53.2 | 47.5 |
| Example A3 | 3.00 | 9.77 | 69.2 | 61.6 |
| Example A4 | 4.08 | 8.08 | 98.8 | 92.3 |
| Example A5 | 5.20 | 5.56 | 96.6 | 88.8 |
| Example A6 | 4.67 | 7.15 | 99.4 | 94.2 |
| Example A7 | 5.24 | 10.38 | 100 | 93.9 |
| Comparative Example A1 | 5.00 | 0 | 18.0 | Trace |
| Comparative Example A2 | 0 | 5.01 | 3.9 | 0 |

Example A8

In a glass reaction tube (volume: 30 mL), 0.309 g of cyclododecanone-O-azacyclotridecen-2-yloxime (0.82 mmol) and 6.17 g of a dioxane solution containing 1.48% by weight of dry HCl (HCl content: 2.47 mmol) were charged under an ambient atmosphere, and the tube was sealed and the reaction was conducted in an oil bath at 90° C. for 10 min.

After the reaction solution was diluted with toluene, products were quantitatively analyzed by high performance liquid chromatography. The results indicated that cyclododecanone oxime was not observed and only laurolactam was formed in a yield of 90.5%.

A yield of laurolactam was determined by the following equation.

Yield of laurolactam (%)=100×(mol number of laurolactam produced)/2×(mol number of cyclododecanone-O-azacyclotridecen-2-yloxime)

Example B1

Process for Producing Cyclododecanone-O-azacyclotridecen-2-yloxime Hydrochloride In 30 g of dichloromethane, 0.6013 g (5.05 mmol) of thionyl chloride was dissolve. Under ice-cooling, 1.9955 g (10.11 mmol) of cyclododecanone oxime was added and dissolved to the solution. Immediately after the dissolution, dichloromethane was removed from this solution by an evaporator to give cyclododecanone-O-azacyclotridecen-2-yloxime hydrochloride as a white powder. The white powder was recrystallized from a mixture of dichloromethane/hexane (mixed solvent: dichloromethane/acetone=4/7 (weight ratio), recrystallization temperature: −10 to −15° C.) to give cyclododecanone-O-azacyclotridecen-2-yloxime hydrochloride as colorless crystals (melting point: 87.4 to 88.9° C.).

The product was identified by elementary analysis, X-ray fluorescence spectroscopy, $^1$H-NMR and $^{13}$C-NMR. The results supported the structure of cyclododecanone-O-azacyclotridecen-2-yloxime hydrochloride. This compound is novel.

(1) Elementary analysis
Observed (%) H, 10.31; C, 70.65, N, 6.16
Calculated (%) H, 10.42; C, 69.82, N, 6.79
(as $C_{24}H_{44}N_2O\cdot HCl$)
(2) X-ray fluorescence spectroscopy
Observed (%) Cl: 8.31
Calculated (%) Cl: 8.61
(as $C_{24}H_{44}N_2O\cdot HCl$)
(3) $^1$H-NMR (400 MHz, $CDCl_3$ solvent)
1.30-1.91 (36H, m), 2.51-2.57 (4H, m), 3.26-3.29 (2H, m), 3.58-3.59 (2H, m), 13.86 (1H, br)
(4) $^{13}$C-NMR (100M Hz, $CDCl_3$ solvent)
22.11, 22.24, 22.56, 23.03, 23.21, 23.52, 23.90, 23.98, 24.88, 24.94, 25.45, 25.50, 25.55, 25.69, 25.99, 26.29, 26.63, 26.92, 29.86, 30.59, 30.83, 43.32, 171.68, 179.52

Example B2

Into a glass reaction tube (volume: 30 mL), 2.0 g of cyclododecanone oxime (10.16 mmol) (Tokyo Chemical Industry Co., Ltd.) was charged under an ambient atmosphere, and then 0.1267 g of cyclododecanone-O-azacyclotridecen-2-yloxime hydrochloride (0.307 mmol, 3.0 mol % of cyclododecanone oxime) and 5.11 g of toluene (Wako Pure Chemical Industries, Ltd.) as a solvent in a glove box under a nitrogen gas atmosphere, and then the tube was sealed and taken out from the glove box. The reaction tube was placed in an oil bath at 105° C. to initiate the reaction. After one hour, the reaction tube was removed from the oil bath and allowed to be cooled.

After the reaction solution was diluted with toluene, products were quantitatively analyzed by high performance liquid chromatography. The results indicated that a conversion of cyclododecanone oxime was 47.2% and a yield of laurolactam was 47.9%.

The analysis conditions of the high performance liquid chromatography were as follows.

Column: J'sphere ODS-H80, column temperature: 40° C., eluent: acetonitrile/water (volume ratio: 55/45), flow rate: 1 mL/min, detection wavelength: 210 nm.

A yield of laurolactam was determined by an absolute calibration curve method according to the following equation.

Yield of laurolactam (%)=100×(mol number of laurolactam produced)/{(mol number of cyclododecanone oxime)+2×(mol number of cyclododecanone-O-azacyclotridecen-2-yloxime hydrochloride)}

Example B3

A procedure was conducted as described for Example B2 except that the amount of cyclododecanone-O-azacyclotridecen-2-yloxime hydrochloride was 5.02 mol % of cyclododecanone oxime. The results are shown in Table 2.

Example B4

A procedure was conducted as described for Example B2 except that the amount of cyclododecanone-O-azacyclotridecen-2-yloxime hydrochloride was 4.09 mol % of cyclododecanone oxime. The results are shown in Table 2.

TABLE 2

| | Cyclododecanone-O-azacyclotridecen-2-yloxime hydrochloride/cyclododecanone oxime (mol %) | Reaction results | |
|---|---|---|---|
| | | Conversion of Cyclododecanone oxime (%) | Yield of laurolactam (%) |
| Example B2 | 3.0 | 47.2 | 47.9 |
| Example B3 | 5.02 | 100 | 101.1 |
| Example B4 | 4.09 | 87.4 | 84.9 |

Example B5

In 50 mL of acetonitrile, 7.0 mg of cyclododecanone-O-azacyclotridecen-2-yloxime hydrochloride was dissolved, and the mixture was reacted at room temperature for 24 hours.

Products were quantitatively analyzed by high performance liquid chromatography. The results indicated that a conversion of cyclododecanone-O-azacyclotridecen-2-yloxime hydrochloride was 100% and a yield of laurolactam was 94.1%.

In Examples C1 to C4 and Comparative Example C1 below, cyclododecanone-O-azacyclotridecen-2-yloxime produced as described in Example A1 was used.

Example C1

In a glass reaction tube (volume: 30 mL), 1.0 g of cyclododecanone oxime (Tokyo Chemical Industry Co., Ltd.) (5.08 mmol) were charged under an ambient atmosphere, and then were added 0.0961 g of bismuth chloride ($BiCl_3$) (Wako Pure Chemical Industries, Ltd.) (6.01 mol % of cyclododecanone oxime), 0.0573 g of cyclododecanone-O-azacyclotridecen-2-yloxime (3.00 mol % of cyclododecanone oxime) and 5.0 g of toluene (Wako Pure Chemical Industries, Ltd.) as a solvent in a globe box of nitrogen gas atmosphere, and the reaction tube was sealed and taken out from the glove box. The above reaction tube was placed in an oil bath at 105° C. to initiate the reaction. After one hour, the reaction tube was removed from the oil bath and allowed to be cooled.

After the reaction solution was diluted with toluene, products were quantitatively analyzed by high performance liquid chromatography. The results indicated that a conversion of cyclododecanone oxime was 100% and a yield of laurolactam was 93.7%.

The analysis conditions in high performance liquid chromatography are as follows.

Column: J'sphere ODS-H80, column temperature: 40° C., eluent: acetonitrile/water (volume ratio: 55/45), flow rate: 1 mL/min, detection wavelength: 210 nm A yield of laurolactam was determined according to the following equation.

Yield of laurolactam (%)=100×(mol number of laurolactam produced)/{(mol number of cyclododecanone oxime)+2×(mol number of cyclododecanone-O-azacyclotridecen-2-yloxime)}

Example C2

A procedure was conducted as described for Example C1 except that the amounts of cyclododecanone-O-azacyclotridecen-2-yloxime and $BiCl_3$ were 5.00 mol % and 10.04 mol % of cyclododecanone oxime, respectively. The results are shown in Table 3.

Example C3

A procedure was conducted as described for Example C1 except that the amounts of cyclododecanone-O-azacyclotridecen-2-yloxime and $BiCl_3$ were 1.00 mol % and 2.06 mol % of cyclododecanone oxime, respectively. The results are shown in Table 3.

Example C4

A procedure was conducted as described for Example C1 except that stannic chloride ($SnCl_4$) was used as a Lewis acid and the amounts of cyclododecanone-O-azacyclotridecen-2-yloxime and $SnCl_4$ were 3.00 mol % and 6.38 mol % of cyclododecanone oxime, respectively. The results are shown in Table 3.

Comparative Example C1

A procedure was conducted as described for Example C1 except that a Lewis acid was absent and the amount of cyclododecanone-O-azacyclotridecen-2-yloxime was 5.00 mol % of cyclododecanone oxime. The results are shown in Table 3.

Comparative Example C2

A procedure was conducted as described for Example C1 except that cyclododecanone-O-azacyclotridecen-2-yloxime was absent and only $BiCl_3$ (6.05 mol % of cyclododecanone oxime) was added. The results are shown in Table 3.

In Examples D1 to D7 and Comparative Example D2 below, cyclododecanone-O-azacyclotridecen-2-yloxime prepared as described in Example A1 was used.

Example D1

In a glass reaction tube (volume: 30 mL), 2.0 g of cyclododecanone oxime (Tokyo Chemical Industry Co., Ltd.) (10.16 mmol) were charged under an ambient atmosphere, and then 0.0146 g of zinc chloride ($ZnCl_2$) (Wako Pure Chemical Industries, Ltd.) (1.05 mol % of cyclododecanone oxime) and 4.6 g of toluene (Wako Pure Chemical Industries, Ltd.) as a solvent in a glove box under a nitrogen-gas atmosphere, and the tube was sealed and taken from the glove box. Separately, in a glove box, 0.242 g of a dioxane solution containing 1.48% by weight of dry HCl (HCl content: 0.239 mmol) and 0.513 g of dichloromethane were added to 0.0841 g of cyclododecanone-O-azacyclotridecen-2-yloxime (0.223 mmol) to prepare a solution (a molar ratio of cyclododecanone-O-azacyclotridecen-2-yloxime to HCl=1.0/1.07), and the vessel was sealed and taken from the glove box. The above reaction tube containing cyclododecanone oxime was placed in an oil bath at 105° C., and after an internal temperature of the reaction tube reached 100° C., 0.418 g of the above solution of cyclododecanone-O-azacyclotridecen-2-yloxime (0.111 mmol of cyclododecanone-O-azacyclotridecen-2-yloxime (1.09 mol % of cyclododecanone oxime) and 0.119 mmol of HCl (1.17 mol % of cyclododecanone oxime)) were injected into the reaction tube by a syringe. After one hour, the reaction tube was taken out from the oil bath and allowed to be cooled.

After the reaction solution was diluted with toluene, products were quantitatively analyzed by high performance liquid chromatography. The results are shown in Table 4.

The analysis conditions of the high performance liquid chromatography were as follows.

Column: J'sphere ODS-H80, column temperature: 40° C., eluent acetonitrile/water (volume ratio: 55/45), flow rate: 1 mL/min, detection wavelength: 210 nm.

TABLE 3

| | Cyclododecanone-O-azacyclotridecen-2-yloxime/cyclodo-decanone oxime (mol %) | Lewis acid | Lewis acid/cyclododecanone oxime (mol %) | Conversion of cyclododecanone oxime (%) | Yield of laurolactam (%) |
|---|---|---|---|---|---|
| | | | | Reaction results | |
| Example C1 | 3.00 | $BiCl_3$ | 6.01 | 100 | 93.7 |
| Example C2 | 5.00 | $BiCl_3$ | 10.04 | 100 | 91.9 |
| Example C3 | 1.00 | $BiCl_3$ | 2.06 | 76.7 | 73.5 |
| Example C4 | 3.00 | $SnCl_4$ | 6.38 | 81.0 | 75.0 |
| Comparative Example C1 | 5.00 | — | 0 | 18.0 | Trace |
| Comparative Example C2 | — | $BiCl_3$ | 6.05 | 8.6 | 4.3 |

Example C5

In 50 mL of acetonitrile, 16.0 mg of cyclododecanone-O-azacyclotridecen-2-yloxime (0.043 mmol) and 14.0 mg of bismuth chloride ($BiCl_3$) (Wako Pure Chemical Industries, Ltd.) (0.044 mmol) were dissolved, and the reaction was conducted in an oil bath at 60° C. for 1 hour.

Products were quantitatively analyzed by high performance liquid chromatography. The results indicated that a conversion of cyclododecanone-O-azacyclotridecen-2-yloxime was 100% and a yield of laurolactam was 91.0%.

A yield of laurolactam was determined according to the following equation.

Yield of laurolactam (%)=100×(mol number of laurolactam produced)/{(mol number of cyclododecanone oxime)+2×(mol number of cyclododecanone-O-azacyclotridecen-2-yloxime)}

Example D2

A procedure was conducted as described for Example D1 except that the amounts of cyclododecanone-O-azacyclotridecen-2-yloxime, HCl and ZnCl$_2$ were 1.07 mol %, 1.17 mol % and 0.70 mol % of cyclododecanone oxime, respectively.

After the reaction solution was diluted with toluene, products were quantitatively analyzed by high performance liquid chromatography. The results are shown in Table 4.

Example D3

A procedure was conducted as described for Example D1 except that the amounts of cyclododecanone-O-azacyclotridecen-2-yloxime, HCl and ZnCl$_2$ were 1.01 mol %, 10.91 mol % and 1.14 mol % of cyclododecanone oxime, respectively.

The reaction solution was diluted with toluene and subjected to quantitative analysis for products by high performance liquid chromatography. The results are shown in Table 4.

Example D4

A procedure was conducted as described for Example D1 except that bismuth chloride (BiCl$_3$) was used as a Lewis acid and the amounts of cyclododecanone-O-azacyclotridecen-2-yloxime, HCl and BiCl$_3$ were 0.64 mol %, 0.70 mol % and 1.05 mol % of cyclododecanone oxime, respectively.

After the reaction solution was diluted with toluene, products were quantitatively analyzed by high performance liquid chromatography. The results are shown in Table 4.

Example D5

A procedure was conducted as described for Example D1 except that cobalt chloride (CoCl$_2$) was used as a Lewis acid and the amounts of cyclododecanone-O-azacyclotridecen-2-yloxime, HCl and CoCl$_2$ were 1.01 mol %, 1.03 mol %, 1.18 mol % of cyclododecanone oxime, respectively.

After the reaction solution was diluted with toluene, products were quantitatively analyzed by high performance liquid chromatography. The results are shown in Table 4.

Example D6

A procedure was conducted as described for Example D1 except that antimony pentachloride (Sb Cl$_5$) was used as a Lewis acid and the amounts of cyclododecanone-O-azacyclotridecen-2-yloxime, HCl and SbCl$_5$ were 1.10 mol %, 1.12 mol % and 1.05 mol % of cyclododecanone oxime, respectively.

After the reaction solution was diluted with toluene, products were quantitatively analyzed by high performance liquid chromatography. The results are shown in Table 4.

Example D7

A procedure was conducted as described for Example D1 except that stannic chloride (SnCl$_4$) was used as a Lewis acid and the amounts of cyclododecanone-O-azacyclotridecen-2-yloxime, HCl and SnCl$_4$ were 1.21 mol %, 1.25 mol % and 1.77 mol % of cyclododecanone oxime, respectively.

After the reaction solution was diluted with toluene, products were quantitatively analyzed by high performance liquid chromatography. The results are shown in Table 4.

Comparative Example D1

A procedure was conducted as described for Example D1 except that cyclododecanone-O-azacyclotridecen-2-yloxime and a Lewis acid were absent and only 0.640 g of a dioxane solution containing 1.48% by weight of dry HCl (HCl content: 0.256 mmol, 5.01 mol % of cyclododecanone oxime).

After the reaction solution was diluted with toluene, products were quantitatively analyzed by high performance liquid chromatography. The results are shown in Table 4.

Comparative Example D2

A procedure was conducted as described for Example D1 except that HCl and a Lewis acid were absent and only cyclododecanone-O-azacyclotridecen-2-yloxime (5.00 mol % of cyclododecanone oxime) was added.

After the reaction solution was diluted with toluene, products were quantitatively analyzed by high performance liquid chromatography. The results are shown in Table 4.

TABLE 4

|  | Cyclododecanone-O-azacyclotridecen-2-yloxime (mol %) | Hydrogen chloride (HCl) (mol %) | Lewis acid (mol %) | Reaction results | |
| --- | --- | --- | --- | --- | --- |
|  |  |  |  | Conversion of cyclododecanone oxime (%) | Yield of laurolactam (%) |
| Example D1 | 1.09 | 1.17 | ZnCl$_2$ 1.05 | 100 | 99.6 |
| Example D2 | 1.07 | 1.17 | ZnCl$_2$ 0.70 | 97.4 | 96.1 |
| Example D3 | 1.01 | 10.91 | ZnCl$_2$ 1.14 | 100 | 97.5 |
| Example D4 | 0.64 | 0.70 | BiCl$_3$ 1.05 | 99.8 | 97.3 |
| Example D5 | 1.01 | 1.03 | CoCl$_2$ 1.18 | 90.3 | 85.5 |
| Example D6 | 1.10 | 1.12 | SbCl$_5$ 1.05 | 81.2 | 77.8 |
| Example D7 | 1.21 | 1.25 | SnCl$_4$ 1.77 | 100 | 97.0 |
| Comparative Example D1 | — | 5.01 | — | 3.9 | 0 |
| Comparative Example D2 | 5.00 | — | — | 18.0 | Trace |

In the table, the amount of each compound is a value relative to an amount (mol) of cyclododecanone oxime.

Example D8

In a glass reaction tube (volume: 30 mL), 0.351 g of cyclododecanone-O-azacyclotridecen-2-yloxime (0.93 mmol), 3.44 g of a dioxane solution containing 1.48% by weight of dry HCl (HCl content: 1.40 mmol) and 0.140 g of $ZnCl_2$ (1.03 mmol) were charged under an ambient atmosphere, the tube was sealed and the reaction was conducted in an oil bath at 90° C. for 10 min.

After the reaction solution was diluted with toluene, products were quantitatively analyzed by high performance liquid chromatography. The results indicated that cyclododecanone oxime was not observed and only laurolactam was formed with a yield of 90.1%.

A yield of laurolactam was determined according to the following equation.

Yield of laurolactam (%)=100×(mol number of laurolactam produced)/2×(mol number of cyclododecanone-O-azacyclotridecen-2-yloxime)

In Examples E1 to E7 below, cyclododecanone-O-azacyclotridecen-2-yloxime hydrochloride produced as described in Example B1 was used.

Example E1

In a glass reaction tube (volume: 30 mL), 2.0 g of cyclododecanone oxime (Tokyo Chemical Industry Co., Ltd.) (10.16 mmol) were charged under an ambient atmosphere, and then, 0.0450 g of cyclododecanone-O-azacyclotridecen-2-yloxime hydrochloride (0.109 mmol, 1.07 mol % of cyclododecanone oxime), 0.0512 g of zinc chloride ($ZnCl_2$) (0.111 mmol, 1.09 mol % of cyclododecanone oxime) and 5.00 g of toluene (Wako Pure Chemical Industries, Ltd.) as a solvent in a glove box under a nitrogen-gas atmosphere, and then the tube was sealed and taken out from the glove box. This reaction tube was placed in an oil bath at 104° C. to initiate the reaction. After one hour, the reaction tube was taken out from the oil bath and allowed to be cooled.

After the reaction solution was diluted with toluene, products were quantitatively analyzed by high performance liquid chromatography. The results indicated that a conversion of cyclododecanone oxime was 100% and a yield of laurolactam was 99.9%.

The analysis conditions of the high performance liquid chromatography were as follows.

Column: J'sphere ODS-H80, column temperature: 40° C., eluent acetonitrile/water (volume ratio: 55/45), flow rate: 1 mL/min, detection wavelength: 210 nm.

A yield of laurolactam was determined according to the following equation.

Yield of laurolactam (%)=100×(mol number of laurolactam produced)/{(mol number of cyclododecanone oxime)+2×(mol number of cyclododecanone-O-azacyclotridecen-2-yloxime hydrochloride)}

Example E2

A procedure was conducted as described for Example E1 except that 0.0446 g of cyclododecanone-O-azacyclotridecen-2-yloxime hydrochloride (1.06 mol % of cyclododecanone oxime) and 0.0567 g of antimony pentachloride (1.84 mol % of cyclododecanone oxime) as a Lewis acid were used.

After the reaction solution was diluted with toluene, products were quantitatively analyzed by high performance liquid chromatography. The results are shown in Table 5.

Example E3

A procedure was conducted as described for Example E1 except that 0.0472 g of cyclododecanone-O-azacyclotridecen-2-yloxime hydrochloride (1.13 mol % of cyclododecanone oxime) and 0.0385 g of stannic chloride ($SnCl_4$) (1.44 mol % of cyclododecanone oxime) as a Lewis acid were used.

After the reaction solution was diluted with toluene, products were quantitatively analyzed by high performance liquid chromatography. The results are shown in Table 5.

Example E4

A procedure was conducted as described for Example E1 except that 0.0440 g of cyclododecanone-O-azacyclotridecen-2-yloxime hydrochloride (1.05 mol % of cyclododecanone oxime) and 0.0145 g of cobalt chloride ($CoCl_2$) (1.08 mol % of cyclododecanone oxime) as a Lewis acid were used.

After the reaction solution was diluted with toluene, products were quantitatively analyzed by high performance liquid chromatography. The results are shown in Table 5.

Example E5

A procedure was conducted as described for Example E1 except that 0.0445 g of cyclododecanone-O-azacyclotridecen-2-yloxime hydrochloride (1.06 mol % of cyclododecanone oxime) and 0.0346 g of bismuth trichloride ($BiCl_3$) (1.08 mol % of cyclododecanone oxime) as a Lewis acid were used.

After the reaction solution was diluted with toluene, products were quantitatively analyzed by high performance liquid chromatography. The results are shown in Table 5.

Example E6

A procedure was conducted as described for Example E1 except that 0.0445 g of cyclododecanone-O-azacyclotridecen-2-yloxime hydrochloride (1.06 mol % of cyclododecanone oxime) and 0.0246 g of zinc bromide ($ZnBr_2$) (1.06 mol % of cyclododecanone oxime) as a Lewis acid were used.

After the reaction solution was diluted with toluene, products were quantitatively analyzed by high performance liquid chromatography. The results are shown in Table 5.

Example E7

In a glass reaction tube (volume: 30 mL), 0.453 g of cyclododecanone-O-azacyclotridecen-2-yloxime hydrochloride (1.10 mmol), 0.0082 g of $ZnCl_2$ (0.060 mmol) and 3.00 g of anhydrous acetonitrile (Wako Pure Chemical Industries, Ltd.) as a solvent were charged in a glove box under a nitrogen-gas atmosphere and the tube was sealed. The tube was taken out from the glove box and the reaction was conducted in an oil bath at 90° C. for 10 min.

The reaction solution was subjected to quantitative analysis for products by high performance liquid chromatography. The results indicated that cyclododecanone oxime was not observed and only laurolactam was formed with a yield of 92.5%.

A yield of laurolactam was determined according to the following equation.

Yield of laurolactam (%)=100×(mol number of laurolactam produced)/2×(mol number of cyclododecanone-O-azacyclotridecen-2-yloxime)

Comparative Example E1

A procedure was conducted as described for Example E1 except that cyclododecanone-O-azacyclotridecen-2-yloxime hydrochloride was absent and only BiCl₃ (6.05 mol % of cyclododecanone oxime) was added.

After the reaction solution was diluted with toluene, products were quantitatively analyzed by high performance liquid chromatography. The results are shown in Table 5.

TABLE 5

| | Cyclododecanone-O-azacyclotridecen-2-yloxime hydrochloride/ cyclododecanone oxime (mol %) | Lewis acid | Lewis acid/ cyclododeca-none oxime (mol %) | Reaction results | |
|---|---|---|---|---|---|
| | | | | Conversion of cyclododecanone oxime (%) | Yield of laurolactam (%) |
| Example E1 | 1.07 | ZnCl₂ | 1.09 | 100 | 99.9 |
| Example E2 | 1.06 | SbCl₅ | 1.84 | 77.4 | 74.3 |
| Example E3 | 1.13 | SnCl₄ | 1.44 | 99.4 | 99.0 |
| Example E4 | 1.05 | CoCl₂ | 1.08 | 62.8 | 59.8 |
| Example E5 | 1.06 | BiCl₃ | 1.08 | 94.6 | 93.7 |
| Example E6 | 1.06 | ZnBr₂ | 1.06 | 65.4 | 65.0 |
| Comparative Example E1 | 0 | BiCl₃ | 6.05 | 8.6 | 4.3 |

Example F1

In a glass mixing unit (volume: 2.5 mL) equipped with a jacket, a 10% by weight of thionyl chloride (rearrangement catalyst) in toluene solution and a 20% by weight of cyclododecanone oxime in toluene solution were fed at 27.7 g/h and 57.5 g/h, respectively, while these were mixed with a stirrer controlling an internal temperature of the mixing unit at 25° C. by the cooling medium in the jacket. A molar ratio of cyclododecanone oxime to thionyl chloride was 2.5. The mixed solution was fed to a glass degassing tank having an internal volume of 48 mL equipped with a jacket through a pipe. A residence time from the mixing unit to the degassing tank was 1.5 min, and a residence time in the degassing tank was 29 min. An internal temperature of the degassing tank was controlled at 35° C. by the cooling medium in the jacket, while the reaction mixture was degassed by nitrogen stream (40 mL/min) with stirring by a stirrer, to initiate pre-preparation and an overflow was allowed to flow down into a rearrangement reaction tank.

On the other hand, to the rearrangement reaction tank, a 50% by weight of cyclododecanone oxime/toluene solution containing 1 mol % of zinc chloride to cyclododecanone oxime was fed at 613 g/h. The rearrangement reaction tank consisted of two CSTRs (Continuous Stirred Tank Flow Reactor) with an internal volume of 163 mL, and a temperature of the heat medium in the jacket was adjusted such that a liquid temperature was 105° C. A reaction time (the total of an average residence time of CSTR 1, 2 tanks) was 0.4 hours, and under the same conditions, a continuous reaction was conducted for continuous 9.5 hours. As a result, a molar generation ratio of a catalytically active species (Formula (2)) in the pre-preparation solution, which was introduced from the degassing tank into the rearrangement reaction tank, to thionyl chloride added in the pre-preparation was 96.2%. Furthermore, a conversion of cyclododecanone oxime in the rearrangement reaction using the pre-preparation solution was 99.97% and a yield of laurolactam was 99.8%. The rearrangement reaction solution thus obtained is not turbid. A molar generation ratio of the catalytically active species (Formula (2)) was calculated on the basis of quantitative analysis by gas chromatography.

Example F2

A pre-preparation and a rearrangement reaction using a pre-preparation solution were conducted as described for Example F1, except that a 20% by weight of cyclododecanone oxime in toluene solution used in pre-preparation was fed at 45.8 g/h and a molar ratio of cyclododecanone oxime to thionyl chloride was 2.0. As a result, a molar generation ratio of a catalytically active species (Formula (2)) in the pre-preparation solution to thionyl chloride added in the pre-preparation was 92.0%. Furthermore, a conversion of cyclododecanone oxime in the rearrangement reaction using the pre-preparation solution was 99.58% and a yield of laurolactam was 99.1%. The rearrangement reaction solution thus obtained was not turbid.

Example F3

A pre-preparation and a rearrangement reaction using a pre-preparation solution were conducted as described for Example F1, except that an internal temperature of a mixing unit was 60° C. As a result, a molar generation ratio of a catalytically active species (Formula (2)) in the pre-preparation solution to thionyl chloride added in the pre-preparation was 96.0%. Furthermore, a conversion of cyclododecanone oxime in the rearrangement reaction using the pre-preparation solution was 99.87% and a yield of laurolactam was 99.6%. The rearrangement reaction solution thus obtained is not turbid.

Comparative Example F1

A pre-preparation and a rearrangement reaction using a pre-preparation solution were conducted as described for Example F1, except that a 10% by weight of thionyl chloride (rearrangement catalyst) in toluene solution was directly fed into a rearrangement reaction tank without conducting pre-preparation. As a result, a conversion of cyclododecanone oxime in the rearrangement reaction was 57.62% and a yield of laurolactam was 56.9%. The rearrangement reaction solution thus obtained was turbid.

Example F4

A pre-preparation and a rearrangement reaction using a pre-preparation solution were conducted as described for Example F1, except that a residence time from a mixing unit to a degassing tank was 200 min. As a result, a molar generation ratio of a catalytically active species (Formula (2)) in the pre-preparation solution to thionyl chloride added in the pre-preparation was 69.0%. Furthermore, a conversion of cyclododecanone oxime in the rearrangement reaction using the pre-preparation solution was 98.70% and a yield of laurolactam was 98.0%. The rearrangement reaction solution thus obtained was not turbid.

Example F5

A pre-preparation and a rearrangement reaction using a pre-preparation solution were conducted as described for Example F1, except that a 20% by weight of cyclododecanone oxime in toluene solution used in the pre-preparation was fed at 34.5 g/h, and a molar ratio of cyclododecanone oxime to thionyl chloride was 1.5. As a result, a molar generation ratio of a catalytically active species (Formula (2)) in the pre-preparation solution to thionyl chloride added in the pre-preparation was 82.8%. Furthermore, a conversion of cyclododecanone oxime in the rearrangement reaction using the pre-preparation solution was 99.36% and a yield of laurolactam was 98.8%. The rearrangement reaction solution thus obtained was not turbid.

Example F6

A pre-preparation and a rearrangement reaction using a pre-preparation solution were conducted as described for Example F1, except that a mixing unit for mixing a 10% by weight of thionyl chloride (rearrangement catalyst) in toluene solution and a 20% by weight of cyclododecanone oxime in toluene solution was based on line mixing solution. Here, a mixing unit temperature was 80° C. and a degassing-tank temperature was 20° C. As a result, a molar generation ratio of a catalytically active species (Formula (2)) in the pre-preparation solution to thionyl chloride added in the pre-preparation was 88.9%. Furthermore, a conversion of cyclododecanone oxime in the rearrangement reaction using the pre-preparation solution was 99.47% and a yield of laurolactam was 99.0%. The rearrangement reaction solution thus obtained was not turbid.

Example F7

A pre-preparation and a rearrangement reaction using a pre-preparation solution were conducted as described for Example F6, except that a degassing-tank temperature was 80° C. As a result, a molar generation rate of a catalytically active species (Formula (2)) in the pre-preparation solution to thionyl chloride added in the pre-preparation was 59.8%. Furthermore, a conversion of cyclododecanone oxime in the rearrangement reaction using the pre-preparation solution was 98.30% while 1% or more of the oxime remained. A yield of laurolactam was 97.5%. The rearrangement reaction solution thus obtained was not turbid.

Example F8

A pre-preparation and a rearrangement reaction using a pre-preparation solution were conducted as described for Example F1, except that a 20% by weight of cyclododecanone oxime in toluene solution used in the pre-preparation was fed at 63.1 g/h, a molar ratio of cyclododecanone oxime to thionyl chloride was 2.75, and an internal temperature of a degassing tank was controlled to 19° C. In this pre-preparation, white crystals were precipitated in the degassing tank.

The crystals thus formed were treated with an alkali and then analyzed by various methods. As a result, it was confirmed that the crystals were cyclododecanone-O-azacyclotridecen-2-yloxime (Formula (1)). Identification was conducted as described in Example A1.

Furthermore, a slurry containing the crystals obtained in the pre-preparation was homogenized and assayed. As a result, a molar generation rate of the catalytically active species (Formula (2)) in the pre-preparation solution to thionyl chloride added in the pre-preparation was 100%.

A rearrangement reaction was conducted using the pre-preparation solution containing the crystals. Resultantly, a conversion of cyclododecanone oxime was 99.98% and a yield of laurolactam was 99.8%. The rearrangement reaction solution thus obtained was not turbid.

The invention claimed is:

1. Cyclododecanone-O-azacyclotridecen-2-yloxime represented by the following formula, its stereoisomer or a mixture thereof

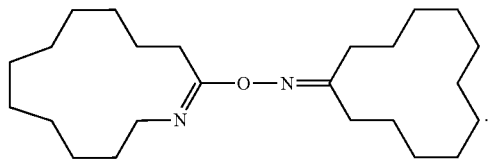 [SMILES: C1CCCCCC(=NO/C2=N/CCCCCCCCCCC2)CCCCC1]

2. Cyclododecanone-O-azacyclotridecen-2-yloxime hydrochloride represented by the following formula, its stereoisomer or a mixture thereof

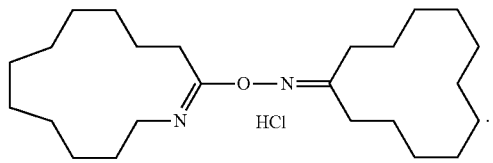

3. A process for producing laurolactam comprising: blending
    (i) cyclododecanone-O-azacyclotridecen-2-yloxime and
    (ii) hydrogen chloride and/or a Lewis acid, and
providing the mixture as a Beckmann rearrangement catalyst and/or a reaction starting material in a reaction step.

4. The process according to claim 3, wherein when hydrogen chloride and a Lewis acid are used, the Lewis acid is a halide of one or two or more metals selected from the group consisting of zinc, cobalt, antimony, tin and bismuth.

5. The process according to claim 3, wherein when hydrogen chloride is absent and a Lewis acid is used, the Lewis acid is a halide of tin and/or bismuth.

6. A process for producing laurolactam comprising providing cyclododecanone-O-azacyclotridecen-2-yloxime hydrochloride as a Beckmann rearrangement catalyst and/or a reaction starting material in a reaction step.

7. The process according to claim 6, further comprising using a Lewis acid.

8. The process according to claim 7, wherein the Lewis acid is a halide of one or two or more metals selected from the group consisting of zinc, cobalt, antimony, tin and bismuth.

9. A process for producing cyclododecanone-O-azacyclotridecen-2-yloxime, comprising:
    blending and dissolving thionyl chloride and cyclododecanone oxime in a two molar amount to thionyl chloride in the presence of a solvent;
    evaporating the solvent;
    adding a solvent; and
    washing the resulting solution with an aqueous alkaline solution until an aqueous layer becomes alkaline.

10. A process for producing cyclododecanone-O-azacyclotridecen-2-yloxime hydrochloride comprising:
blending and dissolving thionyl chloride and cyclododecanone oxime in a two molar amount to thionyl chloride in the presence of a solvent; and
evaporating the solvent.

11. A process for producing laurolactam by a Beckmann rearrangement reaction of an oxime compound using thionyl chloride in a continuous flow apparatus, wherein the oxime compound and thionyl chloride are blended and reacted to form a chlorine-containing catalytically active species.

12. The process according to claim 11, wherein the apparatus comprises a mixing unit, a pipe for a mixed liquid and a degassing tank, wherein the oxime compound and thionyl chloride are blended and reacted in the mixing unit, and a gas generated in the reaction is degassed in the degassing tank.

13. The process according to claim 11, a molar ratio of the oxime compound to thionyl chloride is 2 or more.

14. The process according to claim 11, wherein a reaction temperature is a temperature of the Beckmann rearrangement reaction or lower.

\* \* \* \* \*